United States Patent
Taylor et al.

(10) Patent No.: US 8,129,622 B2
(45) Date of Patent: Mar. 6, 2012

(54) INSULATOR FOR FEEDTHROUGH

(75) Inventors: William John Taylor, Anoka, MN (US); Brad C. Tischendorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 401 days.

(21) Appl. No.: 12/469,823

(22) Filed: May 21, 2009

(65) Prior Publication Data

US 2009/0229858 A1    Sep. 17, 2009

Related U.S. Application Data

(63) Continuation-in-part of application No. 11/949,005, filed on Nov. 30, 2007.

(60) Provisional application No. 60/868,007, filed on Nov. 30, 2006.

(51) Int. Cl.
*H01B 17/26* (2006.01)

(52) U.S. Cl. .......... 174/152 GM; 174/50.61; 174/50.63; 174/50.64; 501/73; 501/77; 501/78; 65/36; 429/180; 429/181; 429/183; 429/184

(58) Field of Classification Search ........... 174/152 GM, 174/50.61, 50.64; 501/78, 14, 11, 73, 77; 65/36; 429/181, 180, 184
See application file for complete search history.

(56) References Cited

U.S. PATENT DOCUMENTS

| | | | |
|---|---|---|---|
| 2,590,893 A * | 4/1952 | Sanborn ............ 252/520.2 |
| 3,646,405 A | 2/1972 | Wallis et al. | |
| 3,803,875 A | 4/1974 | Root et al. | |
| 3,920,888 A | 11/1975 | Barr | |
| 4,152,540 A | 5/1979 | Duncan et al. | |
| 4,285,730 A | 8/1981 | Sanford et al. | |
| 4,314,031 A | 2/1982 | Sanford et al. | |
| 4,323,654 A | 4/1982 | Tick et al. | |
| 4,420,569 A | 12/1983 | Tick | |
| 4,421,947 A | 12/1983 | Kyle | |
| 4,424,551 A | 1/1984 | Stevenson et al. | |
| 4,528,613 A * | 7/1985 | Stetson et al. ............ 361/321.5 |
| 4,940,858 A | 7/1990 | Taylor et al. | |
| 4,943,686 A | 7/1990 | Kucharek | |
| 5,015,530 A | 5/1991 | Brow et al. | |
| 5,021,307 A * | 6/1991 | Brow et al. ............ 429/184 |
| 5,089,446 A | 2/1992 | Cornelius et al. | |
| 5,104,738 A | 4/1992 | Brow et al. | |
| 5,104,755 A | 4/1992 | Taylor et al. | |
| 5,137,849 A * | 8/1992 | Brix et al. ............ 501/15 |

(Continued)

FOREIGN PATENT DOCUMENTS

DE    8631853 U1    11/1988

(Continued)

OTHER PUBLICATIONS

Yourassowsky, E. et al., Combination of minocycline and rifampicin against methicillin- and gentamicin-resistant *Staphylococcus aureus*, J Clin Pathol 1981; 34:559-563.

(Continued)

*Primary Examiner* — Angel R Estrada
*Assistant Examiner* — Dimary Lopez

(57) ABSTRACT

A hermetically sealed microelectromechanical system (MEMS) package for an implantable medical device is presented. The MEMS comprises a first substrate that includes an aperture. A feedthrough assembly is coupled to the aperture; the feedthrough assembly comprises a conductive element housed in a glass insulating member. A second substrate is coupled to the first substrate.

4 Claims, 2 Drawing Sheets

U.S. PATENT DOCUMENTS

| | | | |
|---|---|---|---|
| 5,175,067 A | | 12/1992 | Taylor et al. |
| 5,294,241 A | | 3/1994 | Taylor et al. |
| 5,306,581 A | | 4/1994 | Taylor et al. |
| 5,333,095 A | | 7/1994 | Stevenson et al. |
| 5,648,302 A | * | 7/1997 | Brow et al. ............ 501/50 |
| 5,650,759 A | | 7/1997 | Hittman et al. |
| 5,693,580 A | | 12/1997 | Brow et al. |
| 5,817,984 A | | 10/1998 | Taylor et al. |
| 5,821,011 A | * | 10/1998 | Taylor et al. ............ 429/181 |
| 5,825,608 A | | 10/1998 | Duva et al. |
| 5,851,222 A | | 12/1998 | Taylor et al. |
| 5,866,851 A | | 2/1999 | Taylor et al. |
| 5,867,361 A | | 2/1999 | Wolf et al. |
| 5,870,272 A | | 2/1999 | Seifried et al. |
| 5,871,513 A | | 2/1999 | Taylor et al. |
| 5,902,326 A | | 5/1999 | Lessar et al. |
| 5,922,444 A | * | 7/1999 | Tsuzuki et al. ............ 428/220 |
| 5,977,001 A | * | 11/1999 | Suha et al. ............ 501/66 |
| 6,031,710 A | | 2/2000 | Wolf et al. |
| 6,076,017 A | | 6/2000 | Taylor et al. |
| 6,090,503 A | | 7/2000 | Taylor et al. |
| 6,275,369 B1 | | 8/2001 | Stevenson et al. |
| 6,349,025 B1 | | 2/2002 | Fraley et al. |
| 6,536,882 B1 | | 3/2003 | Hawkins et al. |
| 6,566,978 B2 | | 5/2003 | Stevenson et al. |
| 6,603,182 B1 | | 8/2003 | Low et al. |
| 6,643,903 B2 | | 11/2003 | Stevenson et al. |
| 6,660,116 B2 | | 12/2003 | Wolf et al. |
| 6,759,163 B2 | | 7/2004 | Frysz et al. |
| 6,759,309 B2 | | 7/2004 | Gross |
| 6,768,629 B1 | | 7/2004 | Allen et al. |
| 6,855,456 B2 | | 2/2005 | Taylor et al. |
| 6,888,233 B2 | | 5/2005 | Horning et al. |
| 6,924,165 B2 | | 8/2005 | Horning et al. |
| 7,046,499 B1 | | 5/2006 | Imani et al. |
| 7,094,967 B2 | | 8/2006 | Evans et al. |
| 7,098,117 B2 | | 8/2006 | Najafi et al. |
| 7,210,966 B2 | | 5/2007 | Taylor et al. |
| 7,214,441 B2 | | 5/2007 | Cortright et al. |
| 7,260,434 B1 | | 8/2007 | Lim et al. |
| 7,281,305 B1 | | 10/2007 | Iyer et al. |
| 7,285,509 B2 | | 10/2007 | Bayya et al. |
| 7,964,523 B2 | * | 6/2011 | Mayumi et al. ............ 501/77 |
| 2001/0050837 A1 | | 12/2001 | Stevenson et al. |
| 2003/0083715 A1 | | 5/2003 | Taylor et al. |
| 2003/0123215 A1 | | 7/2003 | Allen et al. |
| 2003/0125185 A1 | | 7/2003 | Hirose |
| 2003/0179536 A1 | | 9/2003 | Stevenson et al. |
| 2004/0126953 A1 | | 7/2004 | Cheung |
| 2004/0152229 A1 | | 8/2004 | Najafi et al. |
| 2004/0180464 A1 | | 9/2004 | Horning et al. |
| 2004/0244484 A1 | | 12/2004 | Horning et al. |
| 2005/0060003 A1 | | 3/2005 | Taylor et al. |
| 2005/0092507 A1 | | 5/2005 | Marshall et al. |
| 2005/0186823 A1 | | 8/2005 | Ring et al. |
| 2006/0009813 A1 | | 1/2006 | Taylor et al. |
| 2006/0173506 A1 | | 8/2006 | Rusin et al. |
| 2006/0247714 A1 | | 11/2006 | Taylor et al. |
| 2006/0290257 A1 | | 12/2006 | Heo et al. |
| 2007/0004580 A1 | | 1/2007 | Kass |
| 2007/0179554 A1 | | 8/2007 | Iyer et al. |
| 2007/0179555 A1 | | 8/2007 | Iyer et al. |
| 2007/0217121 A1 | | 9/2007 | Fu et al. |
| 2007/0234540 A1 | * | 10/2007 | Iyer et al. ............ 29/25.42 |
| 2007/0239223 A1 | | 10/2007 | Engmark et al. |
| 2007/0260282 A1 | | 11/2007 | Taylor et al. |
| 2008/0060844 A1 | | 3/2008 | Teske et al. |
| 2008/0118831 A1 | | 5/2008 | Jouanneau-Si-Larbi et al. |
| 2009/0079517 A1 | | 3/2009 | Iyer |
| 2009/0079518 A1 | | 3/2009 | Iyer |
| 2009/0079519 A1 | | 3/2009 | Iyer |

FOREIGN PATENT DOCUMENTS

| | | |
|---|---|---|
| EP | 0404435 A1 | 12/1990 |
| EP | 0404435 B1 | 9/1996 |

OTHER PUBLICATIONS

Bayston, R. et al., Antimicrobial activity of silicone rubber used in hydrocephalus shunts, after impregnation with antimicrobial substances, J Clin Pathol 1981; 34:1057-1062.

Diemat DM2995PF Series Lead (Pb)-Free Sealing Glass Preforms—Preliminary Data Sheet, Aug. 27, 2006, 4 pages.

Diemat DM2700PF Series, DM2700PF/DM2760PF, Low-Temperature Sealing Glass Preforms—Product Data Sheet, Jul. 24, 2006, 4 pages.

Diemat, Inc. Material Safety Data Sheet—DM2995PF, Aug. 23, 2006, 4 pages.

International Search Report for PCT/US2009/050191 dated Oct. 6, 2009, 4 pages.

International Search Report for PCT/US2008/077179 dated May 25, 2009, 4 pages.

* cited by examiner

INSULATOR FOR FEEDTHROUGH

CROSS-REFERENCE TO RELATED APPLICATIONS

This application is a continuation-in-part of U.S. patent application Ser. No. 11/949,005 filed on Nov. 30, 2007, which claims the benefit of U.S. Provisional Application No. 60/868,007, filed on Nov. 30, 2006. The entire disclosures of each of the above applications are incorporated herein by reference.

FIELD

The present disclosure relates generally to construction of a feedthrough assembly for use in an implantable medical device (IMD), and more particularly, to insulating glass within the feedthrough assembly.

BACKGROUND

This section provides background information related to the present disclosure that is not necessarily prior art.

Numerous devices (e.g., implantable medical devices (IMDs), electrochemical cells (e.g., batteries, capacitors etc.), sensors etc.) are hermetically sealed to prevent liquid from contacting electronic components within the device. A typical feedthrough assembly consists of a conductive element (e.g., wires etc.), a ferrule or sleeve member, an insulating member (e.g., glass, ceramic etc.), and a seal. Feedthroughs include those described in U.S. Pat. Nos. 6,855,456 and 5,175,067 and U.S. Pat. App. Pub. No. 2006/0247714, all to Taylor et al. The ferrule or sleeve member includes an aperture configured to receive the insulating member. A seal may be located between the ferrule or sleeve member and the insulating member. Insulating members include those formed of Ta-23 glass and Cabal-12 glass, as described in U.S. Pat. No. 5,306,581 to Taylor et al. An exemplary feedthrough assembly may be inserted, for example, into a housing of a battery such that a portion of the conductive element extends into the housing to connect with battery elements while another portion of the conductive element extends outside of the housing to connect with other electronic components.

Construction of a feedthrough assembly can require the use of forming weights, complicating production, and in some instances, limiting the minimum feedthrough size. In addition, some insulating members are susceptible to reaction with aqueous solutions, such as body fluids. Reaction with body fluids can erode the insulating member and diminish performance over time. It is desirable to develop improved feedthroughs for IMDs.

SUMMARY

This section provides a general summary of the disclosure, and is not a comprehensive disclosure of its full scope or all of its features.

Glass insulating members and glass performs are provided that comprise about 30% $B_2O_3$; about 30% to about 40% of a member selected from the group consisting of CaO, MgO, SrO, and combinations thereof, with the proviso that the individual amounts of CaO and MgO are each not greater than about 20%; about 5% $La_2O_3$; about 10% $SiO_2$; and about 15% $Al_2O_3$, wherein all percentages are mole percentages. These insulating members and performs are used in feedthrough assemblies and methods of forming feedthrough assemblies.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

Further areas of applicability will become apparent from the description provided herein. The description and specific examples in this summary are intended for purposes of illustration only and are not intended to limit the scope of the present disclosure.

DRAWINGS

Example embodiments will now be described more fully with reference to the accompanying drawings.

DETAILED DESCRIPTION

One embodiment of the invention involves a feedthrough assembly in a microelectromechanical system (MEMS) package. The conductive hermetic feedthrough connects an interior cavity in the MEMS device to another electrononic component or device (e.g., lead interconnect etc.) outside of the MEMs package. The MEMS package may be hermetic and isolated from body fluid contact more so than packages that employ an epoxy attachment to a silicon substrate.

Figure 1:
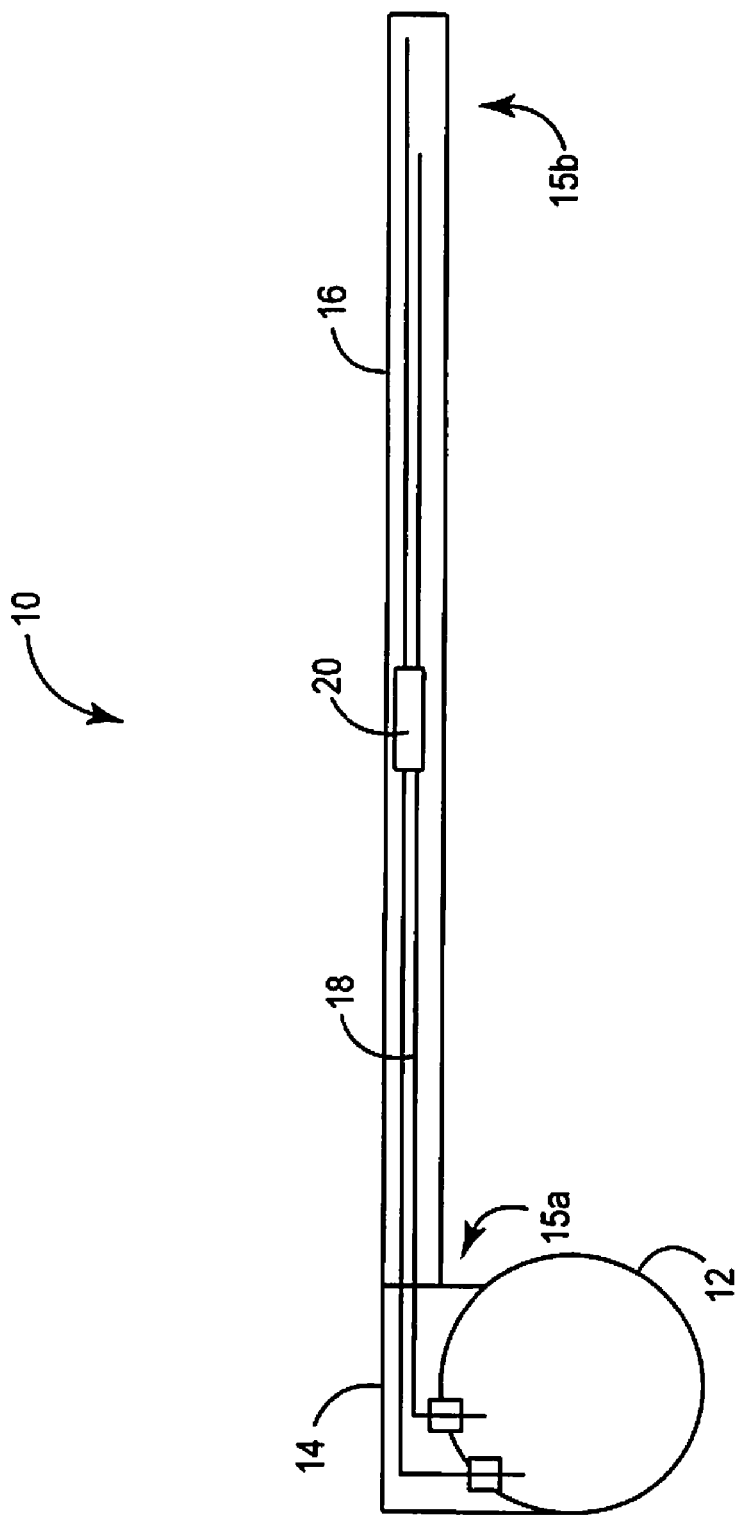
FIG. 1 depicts a schematic view of an implantable medical device.

FIG. 1 depicts a functional unit 20 in a medical device system 10. Functional unit 20 includes a feedthrough assembly (not shown) on or in an integrated circuit (IC), a substrate that includes electronic components (e.g., transistors, logic gates, switches etc.), or a substrate alone. Functional unit 20 can be used anywhere outside the medical device 12 and may be electrically connected to one or more conductor(s) 18. For example, functional unit 20 serves as a sensor (e.g., pressure sensor etc.) that employs a feedthrough assembly.

Medical device system 10 includes a medical device housing 12 having a connector module 14 that electrically couples various internal electrical components of medical device housing 12 to a proximal end 15a of a medical lead 16 such as one or more conductors 18 (e.g., coil, wire etc.) that extend to a distal end 15b of lead 16. Medical device system 10 may comprise any of a wide variety of medical devices that include one or more medical lead(s) 16 and circuitry coupled to the medical lead(s) 16. By way of example, medical device system 10 may take the form of an implantable cardiac pacemaker that provides therapeutic stimulation to the heart or a neurostimulator. Alternatively, medical device system 10 may take the form of an implantable cardioverter, an implantable defibrillator, an implantable cardiac pacemaker-cardioverter-defibrillator (PCD), an implantable pulse generator, or an implantable medical device that solely monitors conditions associated with the patient.

Figure 2:
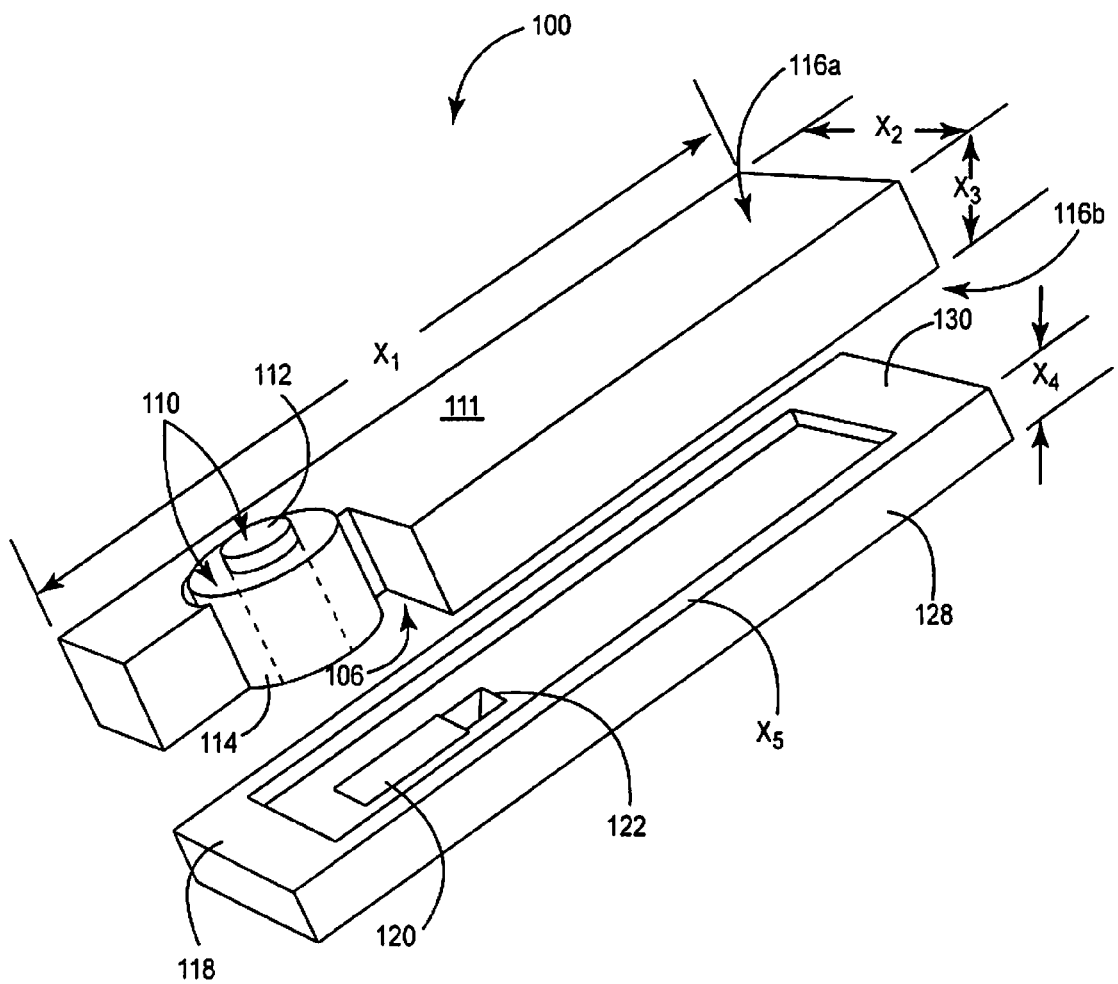
FIG. 2 is a schematic cut away view of a MEMS package that includes a feedthrough assembly.

FIG. 2 illustrates one embodiment of a MEMS package 100 for medical device system 10. MEMS package 100, in one embodiment, may be used in or for a sensor. For example, a MEMS package 100 could be associated with a transducer, which converts a signal into an electrical signal (i.e., voltage, current etc.).

MEMS package 100 includes a feedthrough assembly 110, a first substrate 111, and a second substrate 128. Feedthrough assembly 110 may be hermetically disposed in an aperture 106 of first substrate 111, and coupled to second substrate 128. Feedthrough assembly 110 (e.g., glass-pin-insulatorseal) comprises a conductive element 112 (i.e., pin) hermetically housed in an insulating member 114 (also referred to as sealing glass). Conductive element 112 may be formed of a conductive material, such as tantalum (Ta), niobium (Nb), titanium (Ti), platinum (Pt), iridium (Ir) and/or alloys thereof.

Insulating member 114 may be formed of glass. Typical glass for formation of insulating member 114 comprises boro-alumino, boro-alumino silicate and/or boro silicate type glasses with a wide range of thermal expansions to approximately match biostable conductive element 112 materials such as Ta, Nb, niobium-titanium (Nb—Ti) alloy, Pt, Pt alloys, Ti, alloys of Ti and/or other suitable materials. The element(s) and/or compounds used to form insulating member 114 are selected in a manner to reduce tensile stresses with conductive element 112. For example, insulating member 114, employing glass, has a CTE value about equivalent to or within 15% of the CTE associated with conductive element 110.

The insulating member 114 may be formed from a glass preform. For example, in making a feedthrough assembly 110, the glass preform may be melted so that the molten glass engages conductive element 112 and the inner walls of aperture 106 and subsequently cooled to form insulating member 114. The glass preform has a composition comprising about 30-40% $B_2O_3$, about 0-20% CaO, about 0-20% MgO, about 0-20% SrO, about 0-5% $La_2O_3$, about 5-10% $SiO_2$, and about 10-20% $Al_2O_3$, where all percentages represent mole percents. In some embodiments, the composition further comprises up to about 10% of $MnO_2$, and in some cases the $MnO_2$ may be about 15%. In some embodiments, all or some of the amounts of CaO and/or MgO are replaced with a corresponding amount of SrO, where the amount of SrO does not exceed about 40%. For example, about 10% of CaO and about 5% MgO may be replaced with about 15% SrO. However, the amounts of CaO and MgO are not entirely replaced by SrO, and none of CaO, MgO, and SrO is above 30%. In some embodiments, the composition includes about 30% $B_2O_3$, about 20% CaO, about 20% MgO, about 5% $La_2O_3$, about 10% $SiO_2$, and about 15% $Al_2O_3$.

Various components of the glass composition provide benefits in making a feedthrough assembly 110 and provide the resulting insulating member 114 with advantageous properties. In particular, $La_2O_3$ provides for better glass flow in melting and forming the insulating member 114, as lower temperatures may be employed compared to glass without $La_2O_3$ or with less $La_2O_3$. Lanthanum oxide also increases the coefficient of thermal expansion (CTE) value of the glass. For example, glass with little or no lanthanum oxide may have a CTE of about 6.5, where glass with lanthanum oxide as described herein may have a CTE of about 8.0. The increased CTE values are closer to the CTE values for metals, such as niobium (Nb), titanium (Ti), platinum (Pt), iridium (Ir) and/or alloys thereof. Similar CTE values reduce the resulting compressive force applied to the glass insulating member when disposed within a ferrule (not shown) or the inner walls of aperture 106 upon forming and cooling the feedthrough assembly 110. Excessive force may cause tensile cracks in the glass insulating member 114. The propensity for such tensile cracks may be reduced by employing the present compositions. For example, the present compositions may provide CTE values that are about 10-15% less than the metal of the innerwalls of aperture 106 or of a ferrule.

Strontium oxide within the composition also lowers the processing temperature. For example, as described above, all or some of the amounts of CaO and/or MgO may be replaced with a corresponding amount of SrO. In this way, the processing temperature of the glass composition may be adjusted, for example, in order to offset temperatures necessary to process amounts of silicon dioxide.

The present composition also limits the amount of $SiO_2$ to about 10%, as this amount provides long-term durability but does not substantially increase the processing temperature. For example, $SiO_2$ in the range of 20% or more increases the temperature required for processing the glass to the point where titanium, for example used in conductive element 112, as part of a ferrule, or in the first substrate 111, undergoes a phase transition. This may cause titanium parts, or other metal parts approaching the respective metal or alloy melting temperature, to subsequently warp or become distorted. Thus, the present glass composition keeps the amount of silicon dioxide amount low to allow lower processing temperatures where integrity of titanium portion(s) of the feedthrough assembly 110 are maintained.

The present glass compositions also provide advantageous bonding and sealing between the insulating member 114 and the inner walls of aperture 106 and between the insulating member 114 and conductive element 112. In other embodiments, not shown, the glass composition provides bonding and sealing to a ferrule. The present glass compositions may be used to replace glass insulating members used in feedthroughs as described in U.S. Pat. Nos. 6,855,456; 5,306,581; and 5,175,067; and in U.S. Pat. App. Pub. No. 2006/0247714, all to Taylor et al., the disclosures of which are each incorporated herein by reference.

Conductive element 112 and first substrate 111 are hermetically joined by the insulator material (e.g., glass etc.) of insulating member 114 flowing and engaging conductive element 112 and the inner walls of aperture 106. The hermetic seal could be a coefficient of thermal expansion (CTE) value match, or an approximate match (i.e., CTE within 10%) for all MEMS package components. In another embodiment, the CTE may be within 5% for all MEMS package components. In another embodiment, the CTE may be within 2.5% for all MEMS package components. In yet another embodiment, first substrate 111 (i.e., housing) possesses a CTE greater than insulating member 114 and conductor 112, thereby forming a compression seal.

The present disclosure also provides methods of forming a feedthrough assembly 110. A glass preform may be positioned around a portion of an electrically conductive element 112. The glass preform may comprise the compositions as described herein. At least a portion of the glass preform may be positioned within an aperture 106 of a substrate 111 or within a sleeve member. The glass preform may be softened or fully melted to form a glass insulating member 114 having a sealing engagement with the electrically conductive element 112 and having a sealing engagement with the aperture 106 of the substrate 111 or the sleeve member. In some embodiments, softening or fully melting the glass preform to form a glass insulating member 114 having a sealing engagement with the electrically conductive element 112 and having a sealing engagement with the aperture 106 of the substrate 111 or the sleeve member does not require the use of one or more forming weights. In some embodiments, softening or fully melting the glass preform does not cause the electrically conductive element 112 to undergo a phase transition and does not cause the substrate 111 or the sleeve member to undergo a phase transition, preventing these components from becoming warped or distorted.

First substrate 111 includes a first surface 116a (also referred to as ceramic or glass housing material), a second surface 116b (i.e., silicon material), length X1, width X2, thickness X3, and an aperture 106 for receiving feedthrough assembly 110. First substrate 111 contains the hermetic seal feedthrough assembly 110 and metallized tracings for establishing an electrical connection to second substrate 128. In one embodiment, first substrate 111 comprises a ceramic or glass having a coefficient thermal expansion (CTE) value equivalent to or greater than feedthrough 110 (i.e., pin/glass assembly).

In one embodiment, first substrate 111 may be comprised of a material that has about an equivalent or greater CTE value than conductive element 112 and glass insulating member 114. First substrate 111 can include a ceramic such as for example, polycrystalline alumina with a CTE of about 8.0, sapphire (e.g., single crystal alumina, etc.) with a CTE of about 8.0, and zirconia with a CTE of about 10. In another embodiment, first substrate 111 or housing may be made of glass instead of a ceramic, and possesses general characteristics such that (1) the glass has a higher melting point than insulating member 114; and/or (2) the glass has about an equivalent or greater CTE value than the sealing glass.

Second substrate 128 includes via 122, a metallized trace 120 and includes electronic components that allow MEMS package 110 to function as a sensor substrate such as a transducer; however, skilled artisans appreciate that the substrate may be configured to include any type of circuitry such as switches, signal processing capability, and/or any other suitable form of circuitry related to an implantable medical devices. Second substrate 128 possesses about the same or similar dimensions as first substrate 111. For example, thickness X4 may be the same or about the same as X3. Wall thickness X5 forms a perimeter on the first surface 130 of second substrate 128. The second surface (not shown) of second substrate 128 may be directly adjacent to the housing of an implantable medical device.

Feedthrough assembly 110, disposed in first substrate 111, may then be coupled through joint 118 (e.g., a frit joint etc.) to second substrate 128 (also referred to as a silicon MEMS substrate). Coupling of first substrate 111 to the second substrate 128 may be achieved by use of a glass frit, an Au-silicon eutectic material or other suitable material 118. Second substrate 128 (silicon) material generally has a higher melting point than the glass used to create to a glass insulating member 114. Conductive element 110 may be electrically connected to second substrate 128 through a metal tracing 120. In one embodiment, the metal tracing 120 may be located, for example, in second substrate 128.

Table 1, presented below, provides exemplary dimensions for components of MEMS package 100; however, skilled artisans appreciate that other dimensions may also be used.

TABLE 1

Exemplary dimensions for components of MEMS package.

| Component | Dimension millimeters (mm) |
| --- | --- |
| Conductive element 112 diameter | 0.40 |
| Glass insulating member 114 diameter | 0.75 |
| length X1 | 3.50 |
| width X2 | 1.00 |
| thickness X3 | 0.40 |
| thickness X4 | 0.25 |
| Wall X5 | 0.25 |

Skilled artisans understand other embodiments may implement the principles described herein. For example, a functional unit 20 may be placed in a free body such as a lead. Additionally, while MEMS package is described relative to a sensor or a sensor component (i.e., transducer etc.), it is contemplated that MEMS package 100 can be used in a variety of ways to achieve certain functions of implantable medical devices.

What is claimed is:

1. A feedthrough assembly comprising:
a element for conducting electrical current;
a glass insulating member positioned around a portion of the element, the glass insulating member being in sealing engagement therewith, the glass insulating member comprising: about 30% $B_2O_3$; about 30% to about 40% of a member selected from the group consisting of CaO, MgO, SrO, and combinations thereof, with the proviso that the individual amounts of CaO and MgO are each not greater than about 20%; about 5% $La_2O_3$; about 10% $SiO_2$; and about 15% $Al_2O_3$, wherein all percentages are mole percentages; and
one of:
a sleeve member positioned around the insulating member, the sleeve member in sealing engagement with the insulating member, and
a substrate having an aperture, the insulating member positioned within the aperture and in sealing engagement with the substrate.

2. The feedthrough assembly of claim 1, wherein the glass insulating member further comprises up to about 10% $MnO_2$.

3. The feedthrough assembly of claim 1, wherein the glass insulating member comprises about 30% $B_2O_3$, about 10% CaO, about 15% MgO, about 15% SrO, about 5% $La_2O_3$, about 10% $SiO_2$, and about 15% $Al_2O_3$.

4. The feedthrough assembly of claim 1, wherein one of a sleeve member positioned around the insulating member, the sleeve member in sealing engagement with the insulating member, and a substrate having an aperture, the insulating member positioned within the aperture and in sealing engagement with the substrate, is a substrate that comprises a ceramic or a glass.

* * * * *